(12) United States Patent
Ransbury et al.

(10) Patent No.: US 9,126,048 B2
(45) Date of Patent: Sep. 8, 2015

(54) NEUROMODULATION SYSTEMS AND METHODS FOR TREATING ACUTE HEART FAILURE SYNDROMES

(71) Applicant: Synecor LLC, Chapel Hill, NC (US)

(72) Inventors: Terrance J Ransbury, Chapel Hill, NC (US); William E Sanders, Chapel Hill, NC (US); Richard S Stack, Chapel Hill, NC (US); Colleen Stack, Chapel Hill, NC (US)

(73) Assignee: INTERVENTIONAL AUTONOMICS CORPORATION, Chapel Hill, NC (US)

( * ) Notice: Subject to any disclaimer, the term of this patent is extended or adjusted under 35 U.S.C. 154(b) by 0 days.

(21) Appl. No.: 14/064,544

(22) Filed: Oct. 28, 2013

(65) Prior Publication Data

US 2014/0052208 A1 Feb. 20, 2014

Related U.S. Application Data

(63) Continuation of application No. PCT/US2012/035712, filed on Apr. 28, 2012.

(60) Provisional application No. 61/480,305, filed on Apr. 28, 2011.

(51) Int. Cl.
*A61N 1/00* (2006.01)
*A61N 1/362* (2006.01)
(Continued)

(52) U.S. Cl.
CPC .............. *A61N 1/3621* (2013.01); *A61N 1/056* (2013.01); *A61N 1/36114* (2013.01); *A61B 5/01* (2013.01);
(Continued)

(58) Field of Classification Search
CPC . A61N 1/3622; A61N 1/3621; A61N 1/3962; A61N 1/056; A61N 1/057; A61N 1/36114; A61N 1/3627; A61B 5/01; A61B 5/0215; A61B 5/024; A61M 2025/0175; A61M 25/0074; A61M 25/0125; A61M 25/0147; A61M 25/04
USPC .......................................................... 607/14
See application file for complete search history.

(56) References Cited

U.S. PATENT DOCUMENTS 4,240,433 A * 12/1980 Bordow ........................ 604/540
5,154,172 A 10/1992 Terry, Jr.
(Continued)

FOREIGN PATENT DOCUMENTS

WO WO 2005/065771 A1 7/2005
WO WO 2007/075593 A1 7/2007
(Continued)

OTHER PUBLICATIONS

Bilgutay et al, Vagal Tuning: a new concept in the treatment of supraventricular arrhythmias, angina pectoris, and heart failure, Journal of Thoracic of Cardiovascular Surgery, 1968, vol. 56, No. 1, 71-82.

(Continued)

*Primary Examiner* — George Manuel

(57) ABSTRACT

A neuromodulation system for treating acute heart failure syndromes includes a first catheter having a parasympathetic therapy element adapted for positioning within a first blood vessel such as a superior vena cava, and a second catheter sympathetic therapy element adapted for positioning with a second, different, blood vessel such as the pulmonary artery. The catheters comprise a system in which one of catheters is slidably disposed over the other of the catheters. The system may further be slidably disposed over a third elongate element such as a Swan-Ganz catheter positionable within a pulmonary artery, such that the Swan-Ganz may be used for monitoring parameters such as blood pressure and cardiac output during neuromodulation therapy. The parasympathetic therapy element is energized to deliver neuromodulation therapy to a parasympathetic nerve fiber such as a vagus nerve, while the sympathetic therapy element is energized to deliver neuromodulation therapy to a sympathetic nerve fiber such as a sympathetic cardiac nerve fiber. For treatment of acute heart failure syndromes, the neuromodulation therapy may be used to lower heart rate and increase cardiac inotropy.

20 Claims, 7 Drawing Sheets

(51) Int. Cl.
*A61N 1/05* (2006.01)
*A61N 1/36* (2006.01)
*A61B 5/01* (2006.01)
*A61B 5/0215* (2006.01)
*A61B 5/024* (2006.01)
*A61M 25/00* (2006.01)
*A61M 25/01* (2006.01)
*A61M 25/04* (2006.01)

(52) U.S. Cl.
CPC ............ *A61B 5/024* (2013.01); *A61B 5/0215* (2013.01); *A61M 25/0074* (2013.01); *A61M 25/0125* (2013.01); *A61M 25/0147* (2013.01); *A61M 25/04* (2013.01); *A61M 2025/0175* (2013.01); *A61N 1/057* (2013.01); *A61N 1/3627* (2013.01)

(56) References Cited

U.S. PATENT DOCUMENTS

| | | |
|---|---|---|
| 5,179,950 A | 1/1993 | Stanislaw |
| 5,269,303 A | 12/1993 | Wernicke |
| 5,304,206 A | 4/1994 | Baker, Jr. |
| 5,531,779 A | 7/1996 | Dahl |
| 5,651,378 A | 7/1997 | Matheny |
| 5,700,282 A | 12/1997 | Zabara |
| 5,707,400 A | 1/1998 | Terry, Jr. |
| 5,913,876 A | 6/1999 | Taylor |
| 5,928,272 A | 7/1999 | Adkins |
| 5,954,761 A | 9/1999 | Machek |
| 6,181,966 B1 | 1/2001 | Nigam |
| 6,292,695 B1 | 9/2001 | Webster, Jr. |
| 6,429,217 B1 | 8/2002 | Pkas |
| 6,445,953 B1 | 9/2002 | Bulkes |
| 6,449,507 B1 | 9/2002 | Hill |
| 6,473,644 B1 | 10/2002 | Terry, Jr. |
| 6,479,523 B1 | 11/2002 | Pkas |
| 6,522,926 B1 | 2/2003 | Kieval |
| 6,529,779 B1 | 3/2003 | Sutton |
| 6,542,774 B2 | 4/2003 | Hill |
| 6,564,096 B2 | 5/2003 | Mest |
| 6,616,624 B1 | 9/2003 | Kieval |
| 6,622,041 B2 | 9/2003 | Terry, Jr. |
| 6,656,960 B2 | 12/2003 | Pkas |
| 6,690,971 B2 | 2/2004 | Schauerte |
| 6,697,676 B2 | 2/2004 | Dahl |
| 6,721,603 B2 | 4/2004 | Zabara |
| 6,748,272 B2 | 6/2004 | Carlson |
| 6,778,854 B2 | 8/2004 | Pkas |
| RE38,705 E | 2/2005 | Hill |
| 6,850,801 B2 | 2/2005 | Kievel |
| 6,885,888 B2 | 4/2005 | Rezai |
| 6,907,285 B2 | 6/2005 | Denker |
| 6,912,419 B2 | 6/2005 | Hill |
| 6,934,583 B2 | 8/2005 | Weinberg |
| 6,937,896 B1 | 8/2005 | Kroll |
| 6,978,174 B2 | 12/2005 | Gelfand |
| 6,985,774 B2 | 1/2006 | Kieval |
| 7,069,070 B2 | 6/2006 | Carlson |
| 7,072,720 B2 | 7/2006 | Pkas |
| 7,110,828 B2 | 9/2006 | Kolberg |
| 7,123,959 B2 | 10/2006 | Cates |
| 7,123,961 B1 | 10/2006 | Kroll |
| 7,139,607 B1 | 11/2006 | Shelchuk |
| 7,142,917 B2 | 11/2006 | Fukui |
| 7,149,574 B2 | 12/2006 | Yun |
| 7,162,303 B2 | 1/2007 | Levin |
| 7,181,288 B1 | 2/2007 | Rezai |
| 7,184,829 B2 | 2/2007 | Hill |
| 7,194,313 B2 | 3/2007 | Libbus |
| 7,225,019 B2 | 5/2007 | Jahns |
| 7,231,260 B2 | 6/2007 | Wallace |
| 7,269,457 B2 | 9/2007 | Shafer |
| 7,277,761 B2 | 10/2007 | Shelchuk |
| 7,299,091 B2 | 11/2007 | Barrett |
| 7,310,552 B2 | 12/2007 | Pkas |
| 7,330,765 B2 | 2/2008 | Haldeman |
| 7,336,997 B2 | 2/2008 | Fukui |
| 7,340,299 B2 | 3/2008 | Pkas |
| 7,363,076 B2 | 4/2008 | Yun |
| 7,386,345 B2 | 6/2008 | Pastore |
| 7,455,753 B2 | 11/2008 | Roth |
| 7,477,945 B2 | 1/2009 | Rezai |
| 7,485,104 B2 | 2/2009 | Kieval |
| 7,486,991 B2 | 2/2009 | Libbus |
| 7,499,744 B2 | 3/2009 | Carlson |
| 7,499,748 B2 | 3/2009 | Moffitt |
| 7,509,166 B2 | 3/2009 | Libbus |
| 7,519,421 B2 | 4/2009 | Denker |
| 7,519,424 B2 | 4/2009 | Dennis |
| 7,532,938 B2 | 5/2009 | Machado |
| 7,555,341 B2 | 6/2009 | Moffitt |
| 7,555,351 B2 | 6/2009 | Zhang |
| 7,561,923 B2 | 7/2009 | Libbus |
| 7,572,226 B2 | 8/2009 | Scheiner |
| 7,596,413 B2 | 9/2009 | Libbus |
| 7,617,003 B2 | 11/2009 | Caparso |
| 7,617,005 B2 | 11/2009 | Demarais |
| 7,620,451 B2 | 11/2009 | Demarais |
| 7,634,317 B2 | 12/2009 | Ben-David |
| 7,643,875 B2 | 1/2010 | Heil, Jr. |
| 7,647,114 B2 | 1/2010 | Libbus |
| 7,647,115 B2 | 1/2010 | Levin |
| 7,653,438 B2 | 1/2010 | Deem |
| 7,676,275 B1 | 3/2010 | Farazi |
| 7,717,948 B2 | 5/2010 | Demarais |
| 7,747,323 B2 | 6/2010 | Libbus |
| 7,756,583 B2 | 7/2010 | Demarais |
| 7,765,000 B2 | 7/2010 | Zhang |
| 7,769,446 B2 | 8/2010 | Moffitt |
| 7,769,470 B1 | 8/2010 | Rezai |
| 7,778,704 B2 | 8/2010 | Rezai |
| 7,778,711 B2 | 8/2010 | Ben-David |
| 7,783,362 B2 | 8/2010 | Whitehurst |
| 7,801,627 B2 | 9/2010 | Haldeman |
| 7,809,447 B2 | 10/2010 | Dreier |
| 7,813,812 B2 | 10/2010 | Kieval |
| 7,833,164 B2 | 11/2010 | Scheiner |
| 7,840,278 B1 | 11/2010 | Pkas |
| 7,853,333 B2 | 12/2010 | Demarais |
| 7,865,237 B2 | 1/2011 | Machado |
| 7,865,249 B2 | 1/2011 | Reddy |
| 7,869,881 B2 | 1/2011 | Libbus |
| 7,873,417 B2 | 1/2011 | Demarais |
| 7,877,146 B2 | 1/2011 | Rezai |
| 7,881,788 B2 | 2/2011 | Fukui |
| 7,885,711 B2 | 2/2011 | Ben-Ezra |
| 7,890,187 B2 | 2/2011 | Hochareon |
| 7,890,188 B2 | 2/2011 | Zhang |
| 7,904,175 B2 | 3/2011 | Scott |
| 7,917,230 B2 | 3/2011 | Bly |
| 7,937,143 B2 | 5/2011 | Demarais |
| 7,949,409 B2 | 5/2011 | Bly |
| 7,962,214 B2 | 6/2011 | Byerman |
| 8,024,050 B2 | 9/2011 | Libbus |
| 8,032,215 B2 | 10/2011 | Libbus |
| 8,046,075 B2 | 10/2011 | Rezai |
| 8,126,560 B2 | 2/2012 | Scheiner |
| 8,412,350 B2 | 4/2013 | Bly |
| 8,532,793 B2 * | 9/2013 | Morris et al. .................. 607/130 |
| 2003/0004549 A1 | 1/2003 | Hill |
| 2003/0229380 A1 | 12/2003 | Adams |
| 2004/0019364 A1 | 1/2004 | Kieval |
| 2004/0176672 A1 | 9/2004 | Silver |
| 2005/0096710 A1 | 5/2005 | Kieval |
| 2005/0149156 A1 | 7/2005 | Libbus |
| 2005/0251238 A1 | 11/2005 | Wallace |
| 2005/0251239 A1 | 11/2005 | Wallace |
| 2005/0288730 A1 | 12/2005 | Deem et al. |
| 2006/0079945 A1 | 4/2006 | Libbus |
| 2006/0229677 A1 | 10/2006 | Moffit |
| 2006/0235474 A1 | 10/2006 | Demarais et al. |
| 2006/0253161 A1 | 11/2006 | Libbus et al. |

(56) References Cited

U.S. PATENT DOCUMENTS

| | | |
|---|---|---|
| 2007/0129763 A1 | 6/2007 | Cates |
| 2007/0142879 A1 | 6/2007 | Greenberg |
| 2007/0191904 A1 | 8/2007 | Libbus |
| 2007/0282412 A1 | 12/2007 | Soltis |
| 2007/0282414 A1 | 12/2007 | Soltis |
| 2007/0288076 A1 | 12/2007 | Bulkes |
| 2007/0293925 A1 | 12/2007 | Zarembo |
| 2008/0009917 A1 | 1/2008 | Rossing |
| 2008/0183259 A1 | 7/2008 | Bly |
| 2008/0183264 A1 | 7/2008 | Bly |
| 2008/0234779 A1 | 9/2008 | Pedersen |
| 2008/0288017 A1 | 11/2008 | Kieval |
| 2008/0312712 A1 | 12/2008 | Penner |
| 2009/0005859 A1 | 1/2009 | Keilman |
| 2009/0036940 A1 | 2/2009 | Wei |
| 2009/0155336 A1 | 6/2009 | Rezai |
| 2009/0171411 A1 | 7/2009 | Machado |
| 2009/0228078 A1 | 9/2009 | Zhang |
| 2009/0248119 A1 | 10/2009 | Libbus |
| 2009/0275997 A1 | 11/2009 | Faltys |
| 2009/0276025 A1 | 11/2009 | Burnes |
| 2009/0318989 A1 | 12/2009 | Tomaschko |
| 2010/0036451 A1 | 2/2010 | Hoffer |
| 2010/0100151 A1 | 4/2010 | Terry, Jr. |
| 2010/0113890 A1 | 5/2010 | Cho |
| 2010/0114254 A1 | 5/2010 | Kornet |
| 2010/0137949 A1 | 6/2010 | Mazgalev |
| 2010/0191304 A1 | 7/2010 | Scott |
| 2010/0204741 A1 | 8/2010 | Tweden |
| 2010/0222832 A1 | 9/2010 | Zhang |
| 2011/0029037 A1 | 2/2011 | Rezai |
| 2011/0098762 A1 | 4/2011 | Rezai |
| 2011/0152877 A1 | 6/2011 | Bly |
| 2011/0152974 A1 | 6/2011 | Rezai |

FOREIGN PATENT DOCUMENTS

| | | |
|---|---|---|
| WO | WO2007/092330 | 8/2007 |
| WO | WO 2008/070189 A2 | 6/2008 |
| WO | WO2008/092246 A1 | 8/2008 |
| WO | WO 2009/075750 A2 | 6/2009 |
| WO | WO 2010/017457 A1 | 2/2010 |
| WO | WO2013/022543 | 2/2013 |

OTHER PUBLICATIONS

Cooper et al, Neural effects on sinus rate and atrioventricular conduction produced by electrical stimulation from a transvenous electrode catheter in the canine right pulmonary artery, Circ. Res. 1980; 46; 48-57.

Koizumi et al, Function significance of coactivation of vagal and sympathetic cardiac nerves, Proc. Natl. Acad. Sci., USA, (1982)79: 2116-2120.

Bernston et al, Autonomic Determinism: The Modes of Autonomic Control, the Doctrine of Autonomic Space, and the Laws of Autonomic Constraint, Psychological Review, 1991, vol. 98, No. 4, 459-487.

Carlson et al, Selective Stimulation of Parasympathetic Nerve Fibers to the Human SA Node, Circulation, 1992: 85: 1311-1317.

Yang et al, Sequence of excitation as a factor in sympathetic-parasympathetic interactions in the heart, Circ. Res., 1992, 71: 898-905.

Thompson, Bradycardia Induced by Intravascular Versus Direct Stimulation of the Vagus Nerve, Ann Thorac. Surg, 1998, 65: 637-42.

Schuarte et al, Ventricular Rate Control During Atrial Fibrillation by Cardiac Parasympathetic Nerve Stimulation: A Transvenous Approach, Journal of the American College of Cardiology, vol. 34, No. 7 (Dec. 1999) p. 2043-50.

Schuarte et al, Catheter Stimulation of Cardiac Parasympathetic Nerves in Humans: A Novel Approach to the Cardiac ANS, Circulation 2001, 104: 2430-2435.

Kawashima et al, The autonomic nervous system of the human heart with special reference to its origin, course, and peripheral distribution, Anat Embryol, 2005, 209: 425-438.

Paton et al, The yin and yang of cardiac autonomic control: Vago-sympathetic interactions revisited, Brain Research Reviews, 2005, 49(3): 555-65.

Berntson et al, Cardiac autonomic balance versus cardiac regulatory capacity, Psychophysiology, 2008, 45: 643-652.

Olshansky, et al, Parasympathetic Nervous System and Heart Failure: Pathophysiology and Potential Implications for Therapy, Circulation 2008, 118: 863-871.

Meyer et al, Augmentation of Left Ventricular Contractility by Cardiac Sympathetic Neural Stimulation, Circ. Res., 2010, 121: 1286-1294.

Brown et al, Long term bradycardia by electrical pacing: a new method for studying heart rate reduction, Cardiovascular Research, 1994; 28: 1774-1779.

Goldberger et al, New technique for vagal nerve stimulation, Journal of Neuroscience Methods 91 (1999), 109-114.

Li et al, Vagal Nerve Stimulation Markedly Improves Long-Term Survival After Chronic Heart Failure in Rats, Circulation 2004; 109-120-124.

Schwartz et al, Long term vagal stimulation in patients with advanced heart failure. First experience in man., European Journal of Heart Failure 10(2008) 884-891.

Nabutovsky et al, Lead Design and Initial Applications of a New Lead for Long-Term Endovascular Vagal Stimulation, PACE, vol. 30, S215-S218. 2007.

Extended European Search Report for EP12777812.4, which corresponds to the present application.

PCT Search Report for PCT/US12/035712, which corresponds to the present application.

PCT Search Report for PCT/US12/046332.

File History for Related U.S. Appl. No. 13/547,035.

File History for Related U.S. Appl. No. 14/151,755.

File History for Related U.S. Appl. No. 13/547,031.

File History for Related U.S. Appl. No. 14/516,734.

PCT Search Report for PCT/US2012/046329.

Supplementary European Search Report for European Application No. 12821988.8, corresponding to PCT/US2012/046332.

Janes et al, Anatomy of Human Extrinsic Cardiac Nerves and Ganglia, Am. J. Cardiol 57: 299-309, 1986.

* cited by examiner

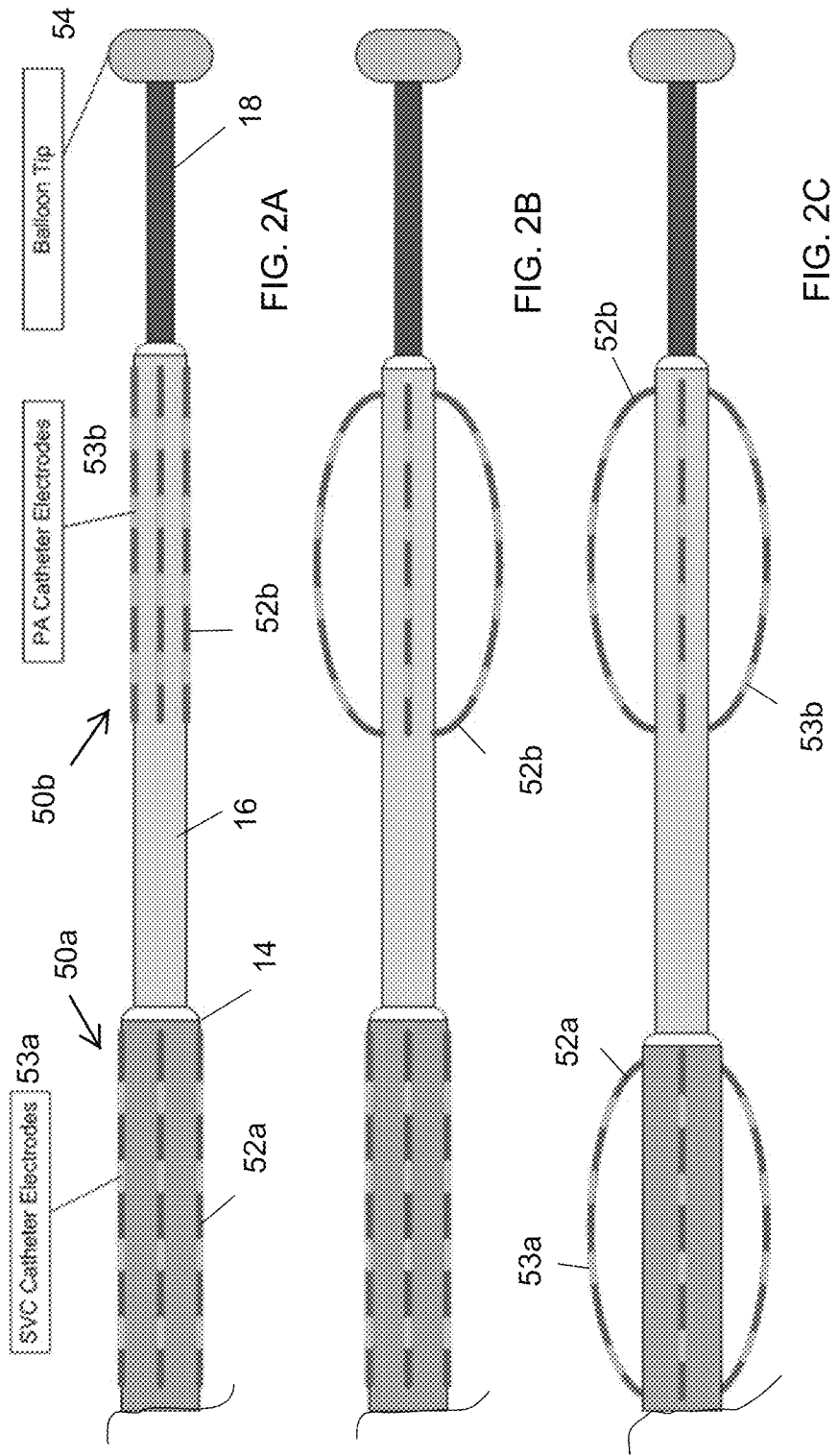

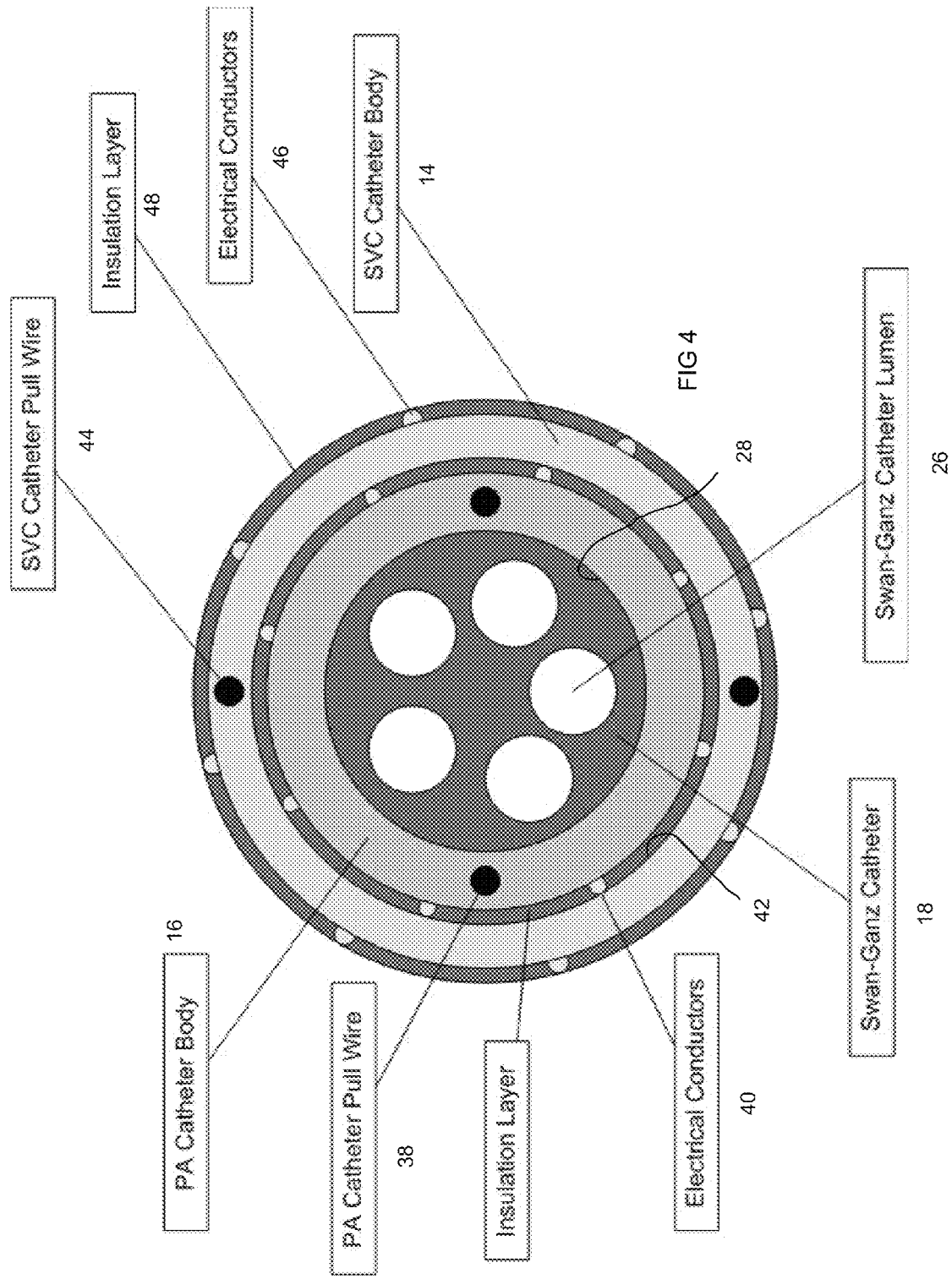

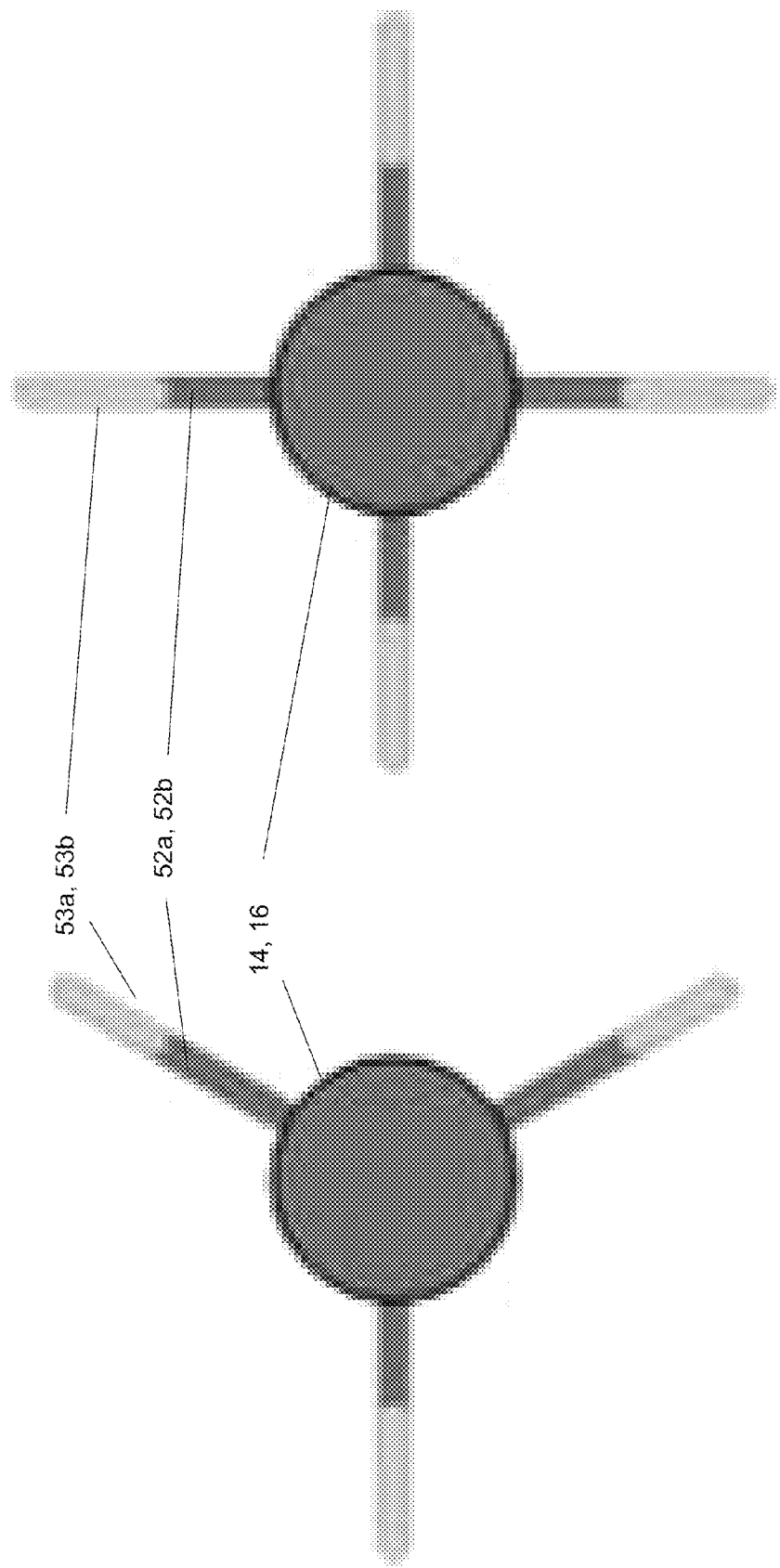

NEUROMODULATION SYSTEMS AND METHODS FOR TREATING ACUTE HEART FAILURE SYNDROMES

The application is a continuation of PCT/US12/35712, filed 28 Apr. 2012, which claims the benefit of U.S. Provisional Application No. 61/480,305, filed 28 Apr. 2011, the entirety of each of which is incorporated herein by reference.

TECHNICAL FIELD OF THE INVENTION

The present application generally relates to systems and methods for treating acute heart failure through augmentation of parasympathetic and sympathetic cardiovascular control.

BACKGROUND

Acute heart failure syndromes (AHFS) are serious conditions resulting in millions of hospitalizations each year. Well documented in the literature are causal links between declining renal function or myocardial injury during AHFS hospitalization and poor prognosis. Heart failure resulting from myocardial ischemic insult or tachycardia precipitates complex alterations in autonomic tone, neurohormonal activation, and the inflammatory metabolic state. These changes in autonomic tone are typically manifested by increased heart rate and a reduction in heart rate variability. In the setting of an acute exacerbation of heart failure, the dramatically elevated heart rate is frequently accompanied by hypotension. The critical role of treating the autonomic nervous system dysfunction observed in HF has long been recognized (with inotropic agents and beta-blockers). Recently, specific neuromodulation of the parasympathetic cardiac nerve inputs has shown significant therapeutic benefit. Cleland J. G., Bristow M. R., Erdmann E, Remme W. J., Swedberg K, Waagstein F. *Beta-blocking agents in heart failure. Should they be used and how?* Eur Heart J 1996;17:1629-39; De Ferrari G. M., Crijns H. J., Borggrefe M, et al. *Chronic vagus nerve stimulation: a new and promising therapeutic approach for chronic heart failure*. Eur Heart J 2011;32:847-55.

However, in the case of AHFS associated with congestive symptoms and reduced blood pressure (BP), the negative inotropic effects of lone parasympathetic intervention or beta-blockade can severely limit their utility. In the face of hypotension, sympathetic tone must be maintained in order to assure adequate left ventricular (LV) contractility. Anand I. S., Fisher L. D., Chiang Y. T., et al. *Changes in brain natriuretic peptide and norepinephrine over time and mortality and morbidity in the Valsartan Heart Failure Trial (Val-HeFT)*. Circulation 2003;107:1278-83. Animal studies have demonstrated positive inotropic effects (increased LV pressure and cardiac output without change in systemic vascular resistance) when selectively stimulating certain cardiac efferent sympathetic nerves. Zarse M, Plisiene J, Mischke K, et al. *Selective increase of cardiac neuronal sympathetic tone: a catheter-based access to modulate left ventricular contractility*. J Am Coll Cardiol 2005;46:1354-9; Meyer C, Rana O. R., Saygili E, et al. *Augmentation of left ventricular contractility by cardiac sympathetic neural stimulation*. Circulation 2010;121:1286-94.

The autonomic nervous system includes the parasympathetic nervous system and the sympathetic nervous system. The parasympathetic and sympathetic nervous system have somewhat opposing effects on the cardiovascular system. One function of the parasympathetic nervous system is to slow the heart through action of the vagus nerve. On the other hand, the sympathetic nervous system is associated with increasing the heart rate and increasing the contractility of the heart. The disclosed system and method augment balance between the sympathetic and parasympathetic systems in AHFS patents so as to lower heart rate and increase heart contractility.

BRIEF DESCRIPTION OF THE DRAWINGS

FIGS. 2A through 2C are side elevation views illustrating a telescoping catheter system for use in the neuromodulation system disclosed in FIG. 1. In FIG. 2A the electrode carrying members of the PA catheter are in the pre-deployment position. In FIG. 2B the electrode carrying member of the PA catheter is in the deployed position, and in FIG. 2C the electrode carrying members of both the PA catheter and the SVC catheter are in the deployed positions.

FIG. 4 is a cross-section view of the shafts of the telescoping SVC, PA and Swan-Ganz catheters of FIG. 2A;

FIGS. 6A and 6B are a distal end view of therapeutic elements, illustrating two examples of splined configurations of the electrode carrying members.

DETAILED DESCRIPTION

Figure 1:
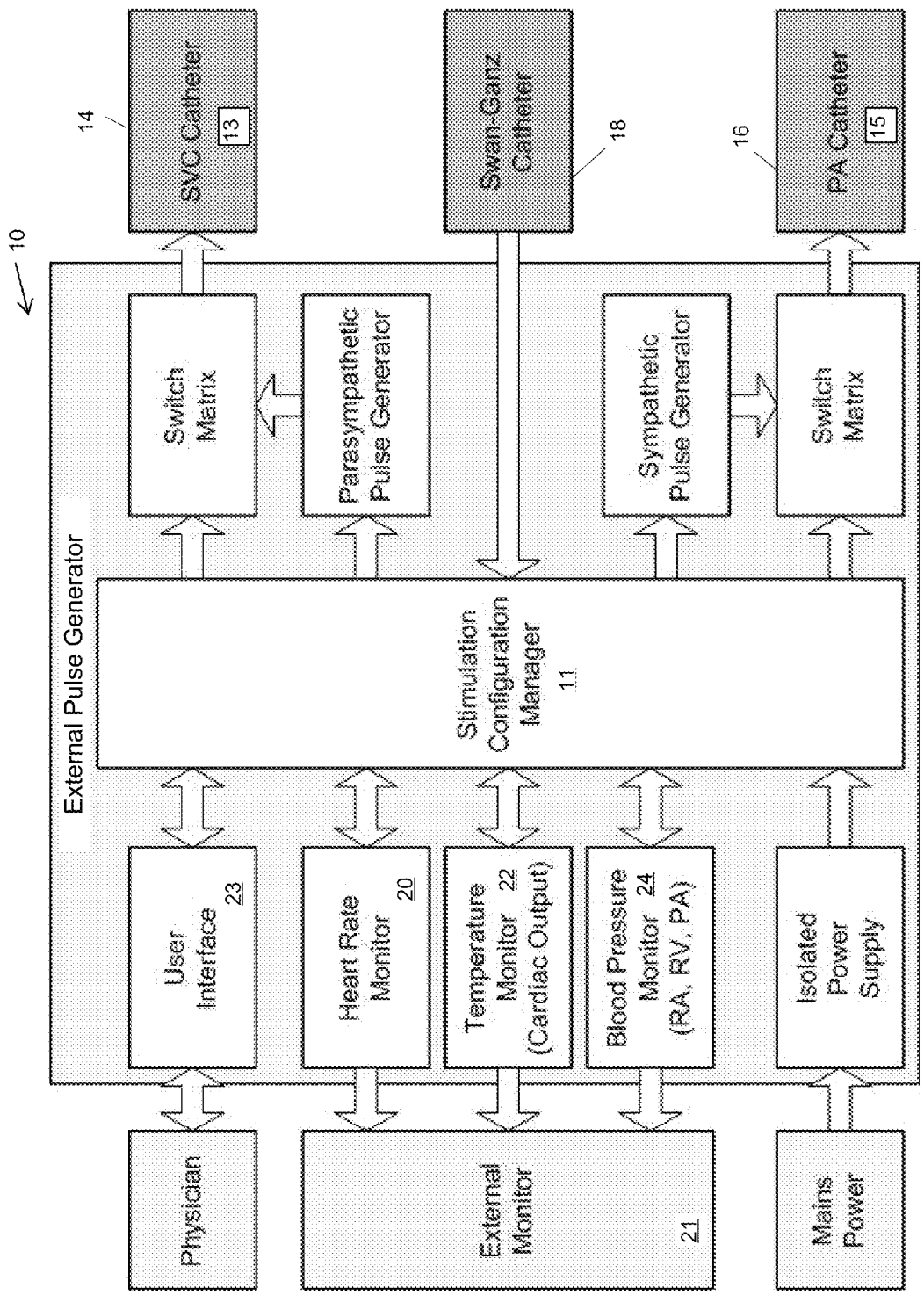
FIG. 1 is a block diagram schematically illustrating an embodiment of an AHFS treatment system.

A neuromodulation system for treating AHFS provides therapeutic elements for simultaneous and/or alternating modulation of parasympathetic and sympathetic fibers to improve autonomic balance in the heart. In preferred embodiments, the therapeutic elements are positioned on one or more catheters positioned in the vasculature of the patient and are energized to modulate nerve fibers positioned outside the vascular walls. Modulation may be carried out to activate and/or inhibit activation of target nerve fibers. In the disclosed system, the therapeutic elements are described as electrodes, although it is contemplated that other forms of therapeutic elements (including, but not limited to, ultrasound, thermal, or optical elements) may instead be used.

The parasympathetic and sympathetic fibers may be modulated from the same therapeutic element or element array, or from difference elements or element arrays. Elements used to modulate sympathetic fibers may be positioned in the same blood vessels as those used for the parasympathetic fibers, or they may be in different blood vessels. The blood vessel and the target position of the therapeutic elements within a chosen vessel is selected based on the vessel's anatomic location relative to the target fiber so as to position the therapeutic element in close proximity to the target fiber while minimize collateral effects. For example, as reported in the literature, in the canine model, right sympathetic fibers modulating left ventricular contractility converge at the common pulmonary artery and course in the pulmonary artery nerves. Left sympathetic fibers modulating ventricular contractility (inotropy) are found near the common pulmonary artery, pulmonary artery nerves, and ventral lateral cardiac nerve. In contrast, sympathetic fibers controlling chronotropic and dromotropic functions are found between the superior vena cava (SVC) and aorta, between the common pulmonary artery and the proximal right pulmonary artery, between the left superior pulmonary vein and the right pulmonary artery, and elsewhere. J. L. Ardell et al, *Differential sympathetic regulation of automatic, conductile, and contractile tissue in dog heart.* The anatomy thus allows a therapeutic element to be positioned to selectively stimulate sympathetic fibers controlling ventricular inotropy to increase contractility, while avoiding chronotropic/dromotropic effects so as not to trigger tachycardia.

In human use, modulation of sympathetic fibers may be achieved using a therapeutic element positioned within the pulmonary artery so as to stimulate sympathetic fibers to increase inotropy. Moreover, therapeutic elements could additionally or alternatively be employed to stimulate parasympathetic fibers that lower heart rate. Such fibers may also be activated using intravascular electrodes located in the pulmonary arteries, although in other embodiments vagal or other parasympathetic fibers are modulated using a therapeutic element in the superior vena cava or the internal jugular vein, preferably on the right side.

In some embodiments, combined or alternating modulation of the parasympathetic and sympathetic fibers may be employed to optimize the opposing effects of parasympathetic and sympathetic modulation on heart rate—such that modulation optimizes the ability of the parasympathetic system to drive the heart rate and the sympathetic system to "apply the brakes" to slow the heart when necessary. Sensed or derived hemodynamic parameters may be used by the system to select and implement stimulation parameters, algorithms and/or to identify the therapeutic element(s) to be activated at a given time. Suitable sensed or derived hemodynamic parameters include pulmonary capillary wedge pressure (PCWP), cardiac index, derivations of vascular resistance, heart rate, blood pressure (arterial). Other parameters may include central venous pressure, CO/CI, and cardiac filling pressures.

FIG. 1 schematically illustrates one embodiment of a system 10 for AHFS treatment. The system includes an external pulse generator/stimulator 12 positioned outside the patient's body. Therapeutic elements are carried by percutaneous catheters that are coupled to the external pulse generator. In the illustrated embodiment, one or more first therapeutic elements 13 are mounted to an SVC catheter 14 for parasympathetic fiber (e.g. vagus nerve) stimulation, and one or more second therapeutic elements 15 are mounted to a pulmonary artery ("PA") catheter 16 for sympathetic fiber stimulation (e.g. sympathetic cardiac nerve fibers). In an alternative embodiment, therapeutic elements on the pulmonary artery catheter are also used for parasympathetic fiber modulation. In such embodiments, the SVC catheter may be eliminated if desired. Where both sympathetic and parasympathetic modulation will be carried out from the same catheter, selection of one fiber (e.g. sympathetic) versus the other (e.g. parasympathetic) might be made by choosing from a plurality of therapeutic elements within an array on that catheter, or by selecting stimulation parameters that will modulate only the target fiber. For example, stimulus might be delivered at a frequency that will modulate the sympathetic fiber but not the parasympathetic fiber when only sympathetic modulation is needed, and then an alternate frequency would be use to modulate the parasympathetic fiber when necessary.

Feedback to stimulation configuration manager 11 of pulse generator/stimulator 12 is provided by one or more diagnostic sensors, including feedback from a Swan-Ganz catheter 18 for determining PCWP as well as other sensors used in the detection/derivation of the parameters disclosed above or indicated in FIG. 1. Some non-limiting examples of sensors are represented in FIG. 1 including a heart rate sensor 20, a temperature sensor 22 that may be used to derive cardiac output, and one or more blood pressure monitors 24 that may be used for right atrial, right ventricular, and/or pulmonary artery pressure monitoring. As known to those skilled in the art, the Swan-Ganz catheter 18 may be used for temperature sensing (employing the thermodilution method of deriving cardiac output), as well as some or all of the pressure monitoring.

An external monitor 21 allows the user to observe sensed or derived parameters. User instructions are input to the stimulation configure manager using user interface 23.

In a preferred embodiment, the system is programmed to integrate hemodynamic and related data in real-time and to control parasympathetic and sympathetic modulation using the therapeutic elements in a manner that maintains favorable hemodynamics. A treatment regimen is preferably automatically selected or calculated by the microprocessor driven system based on the patient's clinical picture. For example, vascular failure (diastolic) might require parasympathetic stimulation to decrease vascular resistance and increase cardiac cycle length, while therapy for cardiogenic shock might require increased cardiac output. In many cases, maximal benefit will be achieved through both sympathetic and parasympathetic modulation either simultaneously or at different times. The therapy could then be titrated as discussed above to optimize sympathetic/parasympathetic balance as the autonomic system does on its own when in the healthy physiologic state.

FIGS. 2A through 2C illustrate an exemplary catheter system for use in neuromodulation of sympathetic and parasympathetic fibers, such as for treatment of AHFS or other conditions. This neuromodulation system includes one or more first intravascular therapeutic elements positionable within the SVC and one or more second intravascular elements positionable within the pulmonary artery. The first therapeutic elements (also referred to herein as the parasympathetic therapeutic elements) are energizable to modulate parasympathetic nerve fibers located outside the vasculature by directing energy to parasympathetic nerve fibers from within the SVC. The second therapeutic elements (referred to as the sympathetic therapeutic elements) are energizable to modulate sympathetic nerve fibers by directing energy to sympathetic nerve fibers from within the pulmonary artery.

In preferred embodiments, the first and second therapeutic elements are electrodes or electrode arrays, although it is contemplated that other forms of therapeutic elements (including, but not limited to, ultrasound, thermal, or optical elements) may instead be used. The therapeutic elements are positioned on flexible catheters.

The catheters include features expandable within the vasculature for biasing the electrodes into contact with the interior surfaces of the blood vessels so as to optimize conduction of neuromodulation energy from the electrodes to the target nerve fibers and to anchor the catheter and electrodes at the desired position for the duration of the treatment. In the embodiments shown, the electrodes on the SVC catheter 14 and the pulmonary artery catheter 16 are carried by electrode carrying members 50a, 50b. Each electrode carrying member has a compressed, streamlined position for pre-deployment passage of the catheter and electrode carrying member through the vasculature during advancement of the electrodes towards the target electrode site. Each electrode carrying member is expandable to an expanded position in which at least a portion of the electrode carrying member is radially deployed towards the interior wall of the blood vessel so as to bias the electrode(s) into contact with the vessel wall.

Figure 2D:
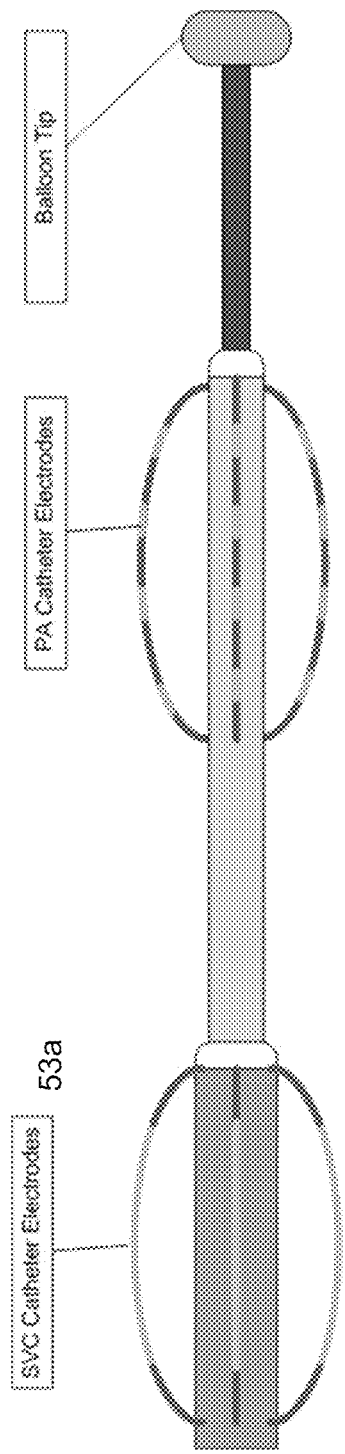
FIG. 2D is similar to FIG. 2C, but shows an alternate electrode configuration on the SVC catheter electrode carrying member.

The drawings show electrode carrying members constructed of spline elements 52a, 52b formed of resilient material such as nitinol, stainless steel, resilient polymer or another resilient material. The spine elements are moveable to a deployed position in a manner known in the art, to cause the spine elements to bow or extend outwardly when the electrode carrying member is moved to the expanded position. Electrodes 53a, 53b are positioned on the spline elements. The electrodes can be the splines themselves, or conductive regions of the splines where the remaining portions of the splines covered or coated with insulative material. Alternatively, electrodes may be attached to the splines, or printed or plated onto the splines. FIGS. 2A-2C show a plurality of spaced apart electrode regions on the splines, while FIG. 2D shows an SVC catheter 14 having a single electrode region 53a on each spline. The number and the arrangement of splines is selected to optimize positioning of the electrodes within the target blood vessel such that when the electrode are energized the target nerve fibers are captured. FIGS. 6A and 6B show distal end views of two electrode carrying members, with the FIG. 6A member having three splines, and the FIG. 6B member having four splines.

In the catheter system illustrated in the drawings, the catheters are designed to be percutaneously introduced (e.g. using access through the femoral vein, subclavian, or internal jugular vein). As shown in FIGS. 2A-2D, FIGS. 3A-3C, and FIG. 4, the catheters may form a telescoping catheter system allowing the Swan-Ganz catheter 18 to be positioned first, with the pulmonary artery catheter 16 then advanced over the Swan-Ganz catheter (i.e. with the shaft of the Swan-Ganz catheter disposed within the lumen of the pulmonary artery catheter), and the SVC catheter 13 then similarly advanced over the pulmonary artery catheter.

Figure 5:
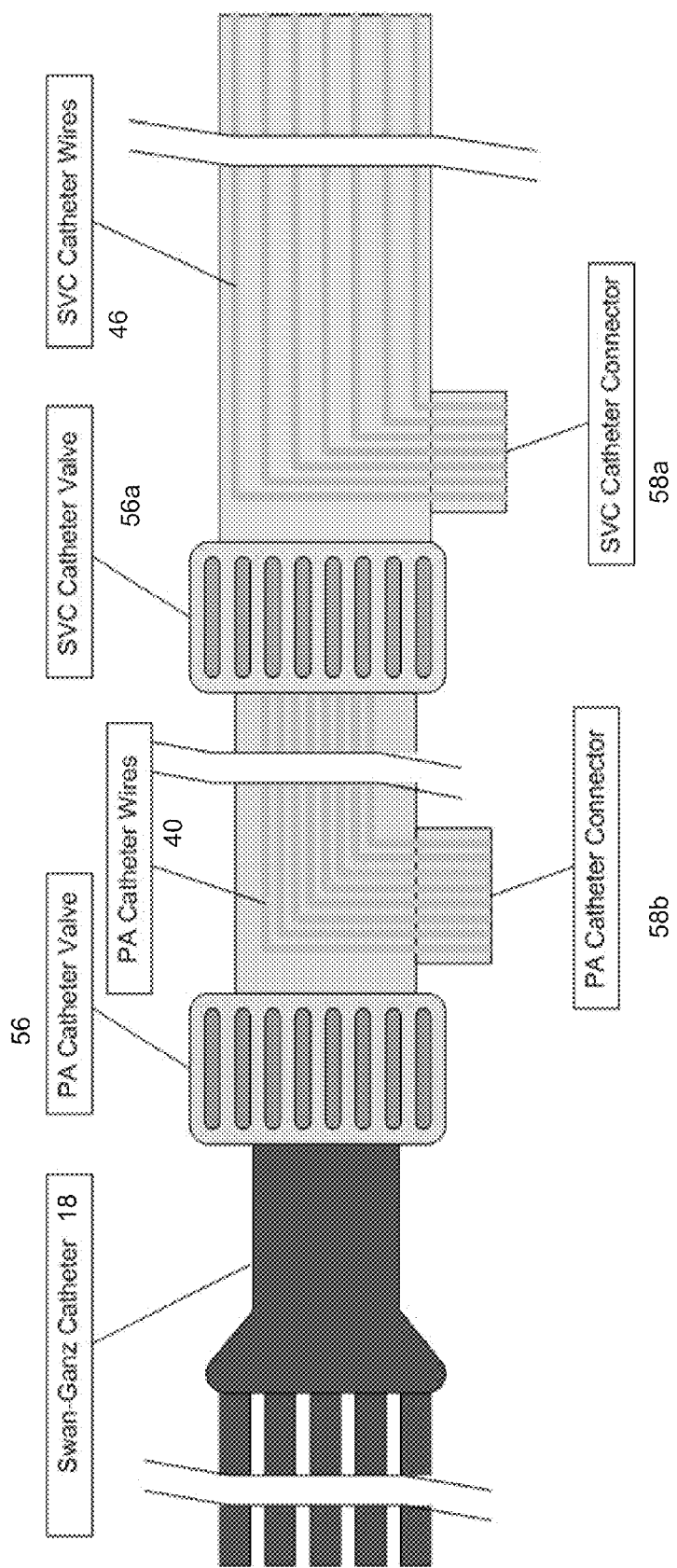
FIG. 5 is a side elevation view showing the proximal ends of the shafts of the telescoping catheters of FIG. 2A.

FIG. 4 is a transverse cross-section view of the telescoping catheter system, with the cross-section taken at a location proximal to the electrode carrying member of the SVC catheter 14. Working from the exterior of the system inwardly, SVC catheter 14 includes a lumen 42 slidable over the exterior of the pulmonary artery catheter 16. If pull-wire deployment is used to move the splines of the SVC catheter to the outwardly-bowed position, pull wires 44 extend through lumens in the walls of the SVC catheter between the spline structure and an actuator disposed at the proximal end of the catheter, which remains outside the body during use. Conductors 46 extend longitudinally through the walls of the catheter (or lumen in those walls). The conductors are electrically coupled to the electrodes 53a (FIG. 2A) at their distal ends, and to a connector 58a (FIG. 5) at their proximal ends.

Pulmonary artery catheter 16 extends through the lumen 42 of the SVC catheter. If pull-wire deployment is used to move the splines of the pulmonary artery catheter to the outwardly-bowed position, pull wires 38 extend through lumens in the walls of the PA catheter between the spline structure and an actuator disposed at the proximal end of the catheter, which remains outside the body during use. Conductors 40 extending through the PA catheter are electrically coupled to the electrodes 53b (FIG. 2B) and to a connector 58b (FIG. 5) at the catheter's proximal end. Extending through the lumen 28 of the PA catheter is the Swan-Ganz catheter 18, which may be a typical multi-lumen 26 Swan-Ganz having a distal balloon 54.

The proximal ends of the three telescoping catheters are illustrated in FIG. 6. The SVC catheter and PA catheter include hemostasis valves 56a, 56b for minimizing blood loss. Each catheter includes connector 58a, 58b that during use is electronically coupled to the pulse generator/stimulator (FIG. 1).

Figure 3C:
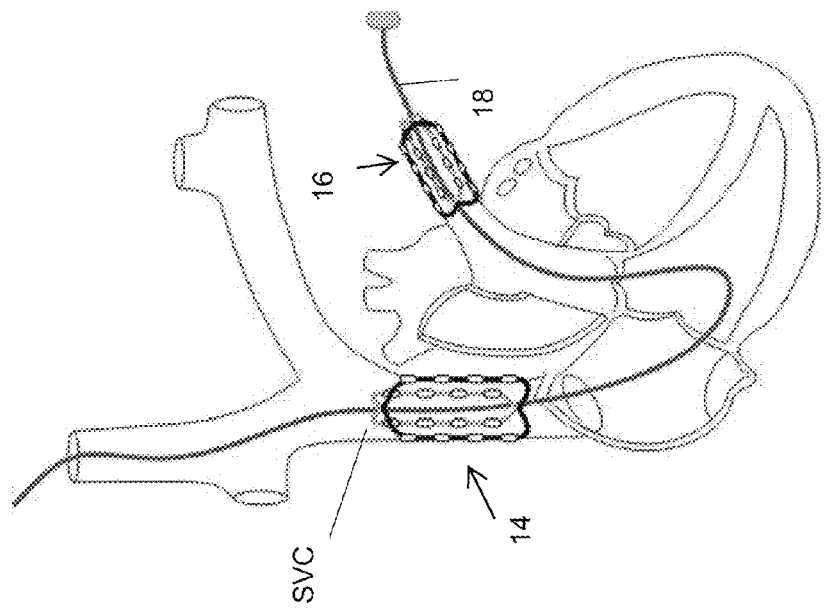
FIGS. 3A-3C are a sequence of drawings schematically illustrating steps useful for advancing the therapeutic components of FIGS. 2A into the heart and surrounding vasculature for delivery of therapy. Note that the shafts of the SVC and PA catheters are not shown in FIGS. 3B and 3C.
Figure 3B:
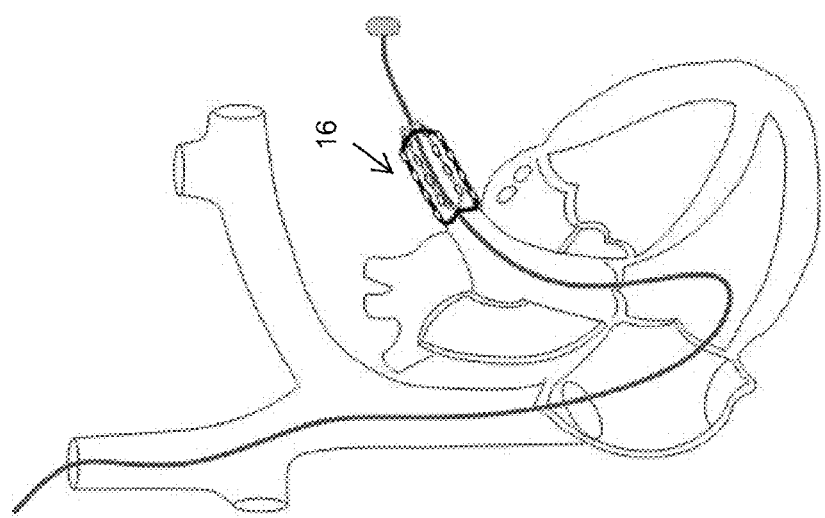
Figure 3A:
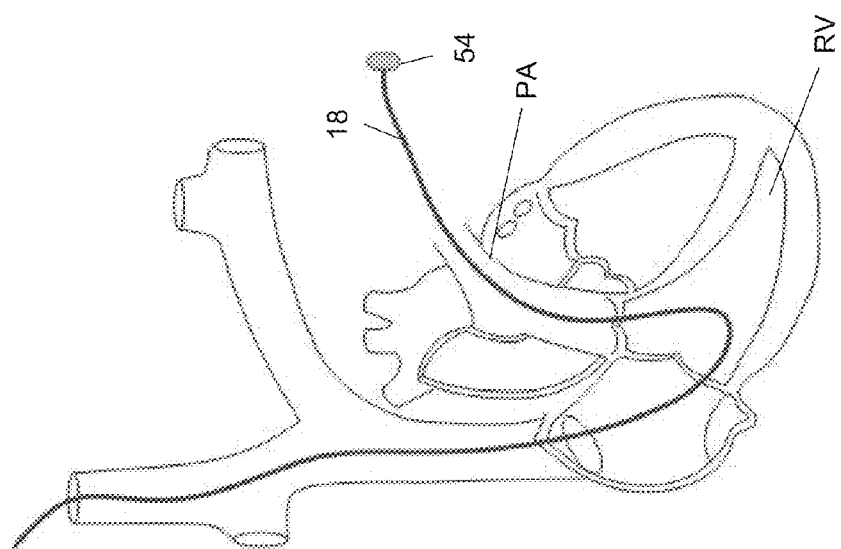

Positioning of the system 10 will next be described with reference to FIGS. 3A-3C. First, Swan-Ganz catheter 18 introduced into the vasculature through a percutaneous incision, and guided to the right ventricle using known techniques. Its balloon tip is inflated, allowing the distal end of the Swan-Ganz to sail with the flow of blood from the right ventricle to the pulmonary artery. FIG. 3A.

Next, the pulmonary artery catheter 16 is advanced over the Swan-Ganz, with the lumen of the PA catheter disposed over the Swan-Ganz, until its electrode carrying member 50b is within the pulmonary artery. The electrode carrying member is expanded within the pulmonary artery (either before or after the SVC catheter is introduced into the SVC), placing the electrodes 53b into contact with the walls of the pulmonary artery. FIG. 3B and 2B.

The SVC catheter 14 is positioned by passing the SVC catheter over the PA catheter and advancing the SVC catheter until its electrode carrying member 50a is within the SVC.

The electrode carrying member is expanded, placing the electrodes 53a into contact with the walls of the SVC. FIG. 3C and 2C.

In a modified method, the PA catheter is advanced into the pulmonary artery using methods besides passage over a Swan-Ganz. For example, the PA catheter could be advanced over another type of catheter or a guidewire introduced into the pulmonary artery.

Once positioned in the vasculature, mapping procedures may be carried out as known in the art to identify the optimal positions of the therapeutic elements within the vasculature. For example, mapping may be used to determine (a) which spline on a given catheter is best positioned to capture the nerve fibers (e.g. the vagus nerve for the SVC catheter and parasympathetic cardiac nerves for the PA catheter) for which neuromodulation is intended, and/or (b) which electrodes on a given spline are in the best position to capture the target nerve fibers, and/or (c) whether the electrode carrying member should be collapsed and repositioned for additional mapping at a second site within the blood vessel. The expandable nature of the distal ends of the SVC and PA catheters temporarily maintains the position of the therapeutic elements at the target sites during the period of time that the patient is undergoing treatment. It bears mention that the spline arrangements are but one example of an expandable electrode carrying member which may be used in the disclosed system. In other embodiments, the telescoping catheters might utilize expandable anchor arrangements such as those of the type disclosed in co-pending U.S. application Ser. No. 13/281,399, entitled Intravascular Electrodes and Anchoring Devices, filed 25 Oct. 2011, which is incorporated herein by reference. Various other forms of temporary anchors may also be used for this purpose, including many that are known in the art for use in cardiac mapping and/or stimulation as well as those used for transvascular nerve stimulation.

We claim:

1. A neuromodulation system for treating a patient, comprising:
    a first catheter having a parasympathetic therapy element adapted for positioning within a first blood vessel;
    a second catheter having a sympathetic therapy element adapted for positioning with a second blood vessel different than the first blood vessel, wherein one of the first and second catheters is slidably disposed within a second one of the first and second catheters;

a stimulator configured to (a) energize the parasympathetic therapy element within the first blood vessel to deliver parasympathetic therapy to a parasympathetic nerve fiber disposed external to the first blood vessel and (b) energize the sympathetic therapy element within the second blood vessel to deliver sympathetic therapy to a sympathetic nerve fiber disposed external to the second blood vessel.

2. The system of claim 1, wherein the stimulator is configured to energize the parasympathetic and sympathetic therapy elements such that delivery of the parasympathetic and sympathetic therapy decreases the patient's heart rate and increases inotropy of the heart of the patient.

3. The system of claim 1, further including control means for controlling the parasympathetic and sympathetic stimulation in response to sensed heart rate and/or blood pressure of the patient.

4. The system of claim 1, wherein each catheter includes an element carrying member, the element carrying members at least partially expandable to position the sympathetic and parasympathetic elements in contact with surrounding vascular walls.

5. The system of claim 1, wherein each therapy element comprises at least one electrode.

6. The system of claim 1, wherein the first catheter is slidably received over the second catheter.

7. The system of claim 6, further including an elongate element percutaneously introducible into the vasculature, wherein the second catheter is slidably received over the elongate element.

8. The system of claim 7, wherein the elongate element is a third catheter.

9. The system of claim 8, wherein the third catheter is a pulmonary artery catheter having sensors thereon.

10. The system of claim 9 wherein the pulmonary artery catheter is a Swan-Ganz catheter.

11. The system of claim 1, wherein the first blood vessel is a superior vena cava, and the second blood vessel is a pulmonary artery.

12. The system of claim 1, wherein the first blood vessel is a venous vessel superior to the heart.

13. The system of claim 12, wherein the first blood vessel is a superior vena cava.

14. The system of claim 12, wherein the second blood vessel is a pulmonary artery.

15. A medical treatment method, comprising the steps of:
percutaneously introducing an elongate member into a vasculature of a patient and positioning a distal portion of the elongate member in a pulmonary artery;
slidably advancing a sympathetic neuromodulation catheter over the elongate member, and positioning a sympathetic therapy element on the sympathetic neuromodulation catheter within the pulmonary artery;
slidably advancing a parasympathetic neuromodulation catheter over the sympathetic neuromodulation catheter member, and positioning a parasympathetic therapy element on the parasympathetic stimulation catheter within the superior vena cava;
modulating at least one parasympathetic nerve fiber using the parasympathetic therapy element disposed within the superior vena cava; and
modulating at least one sympathetic nerve fiber using the sympathetic therapy element a second therapeutic element disposed within the pulmonary artery.

16. The treatment method of claim 15, wherein the elongate member is a Swan-Ganz catheter, and wherein the method further includes monitoring at least one of blood pressure and cardiac output using parameters sensed using the Swan-Ganz catheter.

17. The treatment method of claim 15, wherein the therapy elements are electrodes, and wherein the method includes energizing the electrodes to modulate the nerve fibers.

18. The treatment method of claim 15, wherein at least one of the sympathetic and parasympathetic therapy elements is carried by an element carrying member, and wherein the method includes, within the blood vessel, expanding the element carrying member to position the therapy element into contact with an interior wall of the blood vessel.

19. The treatment method of claim 15, wherein modulating the sympathetic and parasympathetic nerve fibers decreases heart rate and increases inotropy of the patient.

20. The treatment method of claim 19, wherein the sympathetic nerve fiber is a sympathetic cardiac nerve fiber, and wherein the parasympathetic nerve fiber is a vagus nerve fiber.

* * * * *